US00PP28287P3

(12) United States Plant Patent
Beekenkamp

(10) Patent No.: US PP28,287 P3
(45) Date of Patent: Aug. 15, 2017

(54) ***DAHLIA* PLANT NAMED 'BKDADO'**

(50) Latin Name: *Dahlia hybrida*
Varietal Denomination: BKDADO

(71) Applicant: BEEKENKAMP PLANTS B.V., Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 16 days.

(21) Appl. No.: 14/998,421

(22) Filed: Dec. 31, 2015

(65) Prior Publication Data

US 2017/0196151 P1 Jul. 6, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. A. Whealy

(57) ABSTRACT

A new and distinct cultivar of *Dahlia* plant named 'BKDADO', characterized by its broadly upright plant habit; freely basal branching habit; dense and bushy growth habit; medium-sized dark green-colored leaves; and large decorative inflorescences with orange-colored ray florets.

2 Drawing Sheets

Botanical designation: *Dahlia hybrida.*
Cultivar denomination: 'BKDADO'.

BACKGROUND OF THE INVENTION

The present invention relates to a new and distinct cultivar of *Dahlia* plant, botanically known as *Dahlia hybrida* and hereinafter referred to by the name 'BKDADO'.

The new *Dahlia* plant is a product of a planned breeding program conducted by the Inventor in Heinenoord and Maasdijk, The Netherlands. The objective of the breeding program is to create new container *Dahlia* plants that have a freely basal branching habit, and large decorative inflorescences with attractive ray floret coloration.

The new *Dahlia* plant is a naturally-occurring whole plant mutation of *Dahlia hybrida* 'BKDARD', disclosed in U.S. Plant Pat. No. 22,929. The new *Dahlia* plant was discovered and selected by the Inventor as a single flowering plant from within a population of plants of 'BKDARD' in a controlled greenhouse environment in Heinenoord, The Netherlands in August, 2011.

Asexual reproduction of the new *Dahlia* plant by terminal cuttings in a controlled greenhouse environment in Maasdijk, The Netherlands since November, 2011 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDADO'. These characteristics in combination distinguish 'BKDADO' as a new and distinct *Dahlia* plant:

1. Broadly upright plant habit.
2. Freely basal branching habit; dense and bushy growth habit.
3. Medium-sized dark green-colored leaves.
4. Large decorative inflorescences with orange-colored ray florets.

Plants of the new *Dahlia* differ primarily from plants of the mutation parent, 'BKDARD' in ray floret color as plants of 'BKDARD' have bright red-colored ray florets.

Plants of the new *Dahlia* can be compared to plants of *Dahlia hybrida* 'BKDAOR', disclosed in U.S. Plant Pat. No. 23,487. In side-by-side comparisons conducted in Maasdijk, The Netherlands, plants of the new *Dahlia* differed from plants of 'BKDAOR' in the following characteristics:

1. Plants of the new *Dahlia* were more upright than and not as compact as plants of 'BKDAOR'.
2. Plants of the new *Dahlia* were not as freely flowering as plants of 'BKDAOR'.
3. Plants of the new *Dahlia* and 'BKDAOR' differed in ray floret color as plants of 'BKDAOR' had yellow to yellow orange-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDADO' grown in a container.

The photograph on the second sheet is a close-up view of typical inflorescences of 'BKDADO'.

DETAILED BOTANICAL DESCRIPTION

The aforementioned photographs and the following observations and measurements describe plants grown during the autumn in 1.5-liter containers in a glass-covered greenhouse in Maasdijk, The Netherlands and under cultural practices which approximate those generally used in commercial *Dahlia* production. During the production of the plants, day and night temperatures ranged from 17° C. to 19° C. Plants were pinched one time and were eleven weeks old when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDADO'.

Parentage: Naturally-occurring whole plant mutation of *Dahlia hybrida* 'BKDARD', disclosed in U.S. Plant Pat. No. 22,929.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures ranging from 19° C. to 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically white in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Broadly upright and mounding plant form; freely basal branching habit with about four primary branches each with about two secondary branches developing per plant; inflorescences held above the foliar plane on strong peduncles; bushy and dense growth habit; pinching is not required but will improve branching habit.

*Plant height, soil level to top of foliar plane*.—About 18.9 cm.

*Plant height, soil level to top of floral plane*.—About 31.9 cm.

*Plant diameter or spread*.—About 32.2 cm.

*Lateral branches*.—Length: About 13.1 cm. Diameter: About 6 mm. Internode length: About 3.4 cm. Aspect: Primary branches are mostly erect; secondary branches, about 35° from primary branch axis. Strength: Moderately strong. Texture and luster: Smooth, glabrous; glossy. Color, developing: Close to 146A. Color, developed: Close to 143A tinged with close to N186C.

Leaf & leaflet description:

*Arrangement*.—Leaves opposite and compound with three or five leaflets.

*Length, leaves*.—About 16.7 cm.

*Length, leaflets*.—About 7.9 cm.

*Width, leaves*.—About 14.3 cm.

*Width, leaflets*.—About 4.8 cm.

*Shape, leaves in overall outline*.—Ovate.

*Shape, leaflets*.—Ovate.

*Apex, leaflets*.—Acute.

*Base, leaflets*.—Attenuate.

*Margin, leaflets*.—Coarsely serrate.

*Venation pattern, leaflets*.—Pinnate.

*Texture and luster, upper surface, leaflets*.—Slightly rugose, glabrous; slightly velvety; matte.

*Texture and luster, lower surface, leaflets*.—Smooth, glabrous; matte.

*Color*.—Developing leaflets, upper surface: Close to 147A. Developing leaflets, lower surface: Close to 147B. Fully expanded leaflets, upper surface: Slightly darker than between NN137A and 189A; venation, close to 143A. Fully expanded leaflets, lower surface: Close to 191A; venation, close to 147B.

*Petioles*.—Length: About 4.9 cm. Width: About 5 mm. Height: About 5 mm. Strength: Moderately strong to strong. Texture and luster, upper and lower surfaces: Smooth, glabrous; glossy. Color, upper surface: Close to 146A. Color, lower surface: Close to 144A.

Inflorescence description:

*Appearance and arrangement*.—Double inflorescence form with ray and disc florets forming acropetally on a receptacle; inflorescences positioned above and beyond the foliar plane on strong peduncles; inflorescences face mostly upright; freely flowering habit with about 20 inflorescences developing per plant.

*Fragrance*.—None detected.

*Flowering response and flowering period*.—Early flowering habit, plants begin flowering about ten weeks after planting; plants flower continuously during the autumn into the winter in The Netherlands.

*Post-production longevity*.—Inflorescences maintain good substance for about ten days on the plant; inflorescences persistent.

*Inflorescence buds*.—Height: About 7 mm. Diameter: About 1 cm. Shape: Flattened globular. Texture and luster: Smooth, glabrous; glossy. Color: Close to 144B to 144C.

*Inflorescence size*.—Diameter: About 7.4 cm. Depth (height): About 7.8 cm. Disc diameter: About 8 mm, inconspicuous.

*Receptacles*.—Height: About 4 mm. Diameter: About 9 mm. Shape: Flattened globular. Color: Close to 145C.

*Ray florets*.—Quantity per inflorescence and arrangement: About 180 arranged in about eight whorls. Length: About 3.9 cm. Width: About 2 cm. Shape: Broadly obovate. Apex: Obtuse to shallowly retuse. Base: Attenuate. Margin: Entire. Aspect: Upright to roughly horizontal and eventually downward; moderately concave. Texture and luster, upper surface: Smooth, glabrous; moderately velvety; slightly glossy. Texture and luster, lower surface: Smooth, glabrous; moderately velvety; matte. Color: When opening, upper surface: Close to 22A; towards the base, close to 163B. When opening, lower surface: Close to 22A flushed with close to 37C; proximally, close to N45A to N45C. Fully opened, upper surface: Close to 22A and 23B; towards the base, close to 12A; colors becoming closer to 28B and towards the base, close to 9B with development; venation, same as lamina colors. Fully opened, lower surface: Close to 22A flushed with close to 37B; proximally, close to N45B to N45C; colors becoming close to 53C to 53D and towards the apex, close to 8B to 8C with development; venation, same as lamina colors.

*Disc florets*.—Quantity per inflorescence and arrangement: About 30 massed at the center of the inflorescence in about three whorls. Length: About 1.4 cm. Diameter: About 1.5 mm. Shape: Tubular, elongated; apices, acute. Texture and luster, inner and outer surfaces: Smooth, glabrous; glossy. Color, when opening, inner and outer surfaces: Apex: Close to 13A. Mid-section and base: Close to 151C to 151D. Color, fully opened, inner and outer surfaces: Apex: Close to 13A. Mid-section and base: Close to 151C.

*Phyllaries*.—Quantity per inflorescence and arrangement: About eight arranged in about two whorls. Length: About 1.3 cm. Width: About 7 mm. Shape: Ovate. Apex: Acute. Base: Cuneate. Margin: Entire. Texture and luster, upper and lower surfaces: Smooth, glabrous; moderately glossy. Color, upper and lower surfaces: Close to NN137B.

*Peduncles*.—Length, terminal peduncle: About 10.6 cm. Diameter, terminal peduncle: About 3.5 mm. Strength: Strong. Texture and luster: Smooth, glabrous; moderately glossy. Color: Close to 144A; proximally, tinged with close to darker than 148A.

*Reproductive organs*.—Androecium, present on disc florets only: Quantity per floret: About five. Filament length: About 1 mm. Filament color: Close to 151D. Anther shape: Narrowly oblong. Anther length: About 4 mm. Anther color: Close to 200A. Pollen amount: Abundant. Pollen color: Close to 21A. Gynoecium, present on disc florets only: Quantity per floret: One. Pistil length: About 1.3 cm. Style length: About 9 mm. Style color: Close to 151D. Stigma diameter: About 1.5 mm. Stigma shape: Cleft, decurrent. Stigma color: Close to 17A to 17B. Ovary color: Close to 145D. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDADO' as illustrated and described.

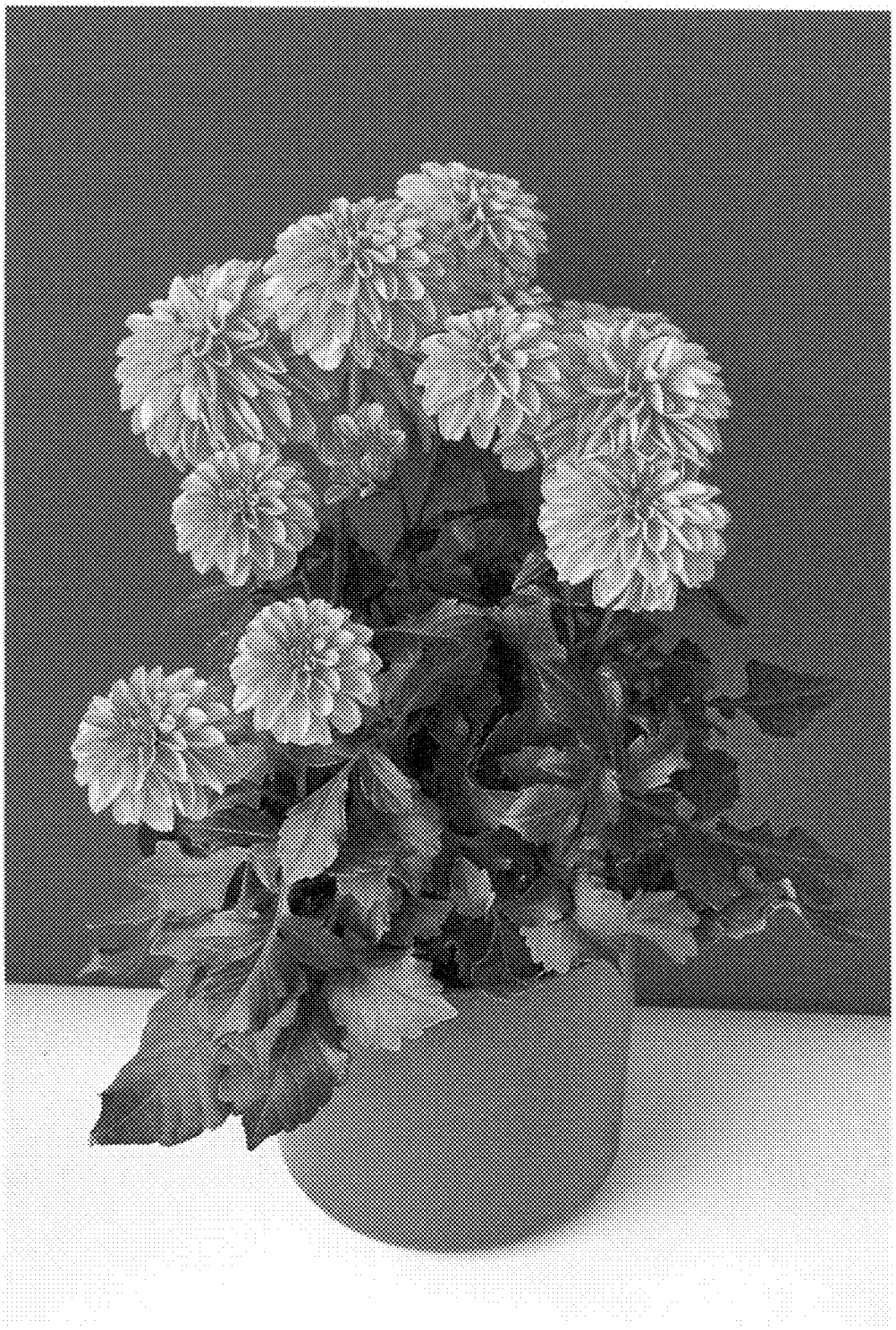

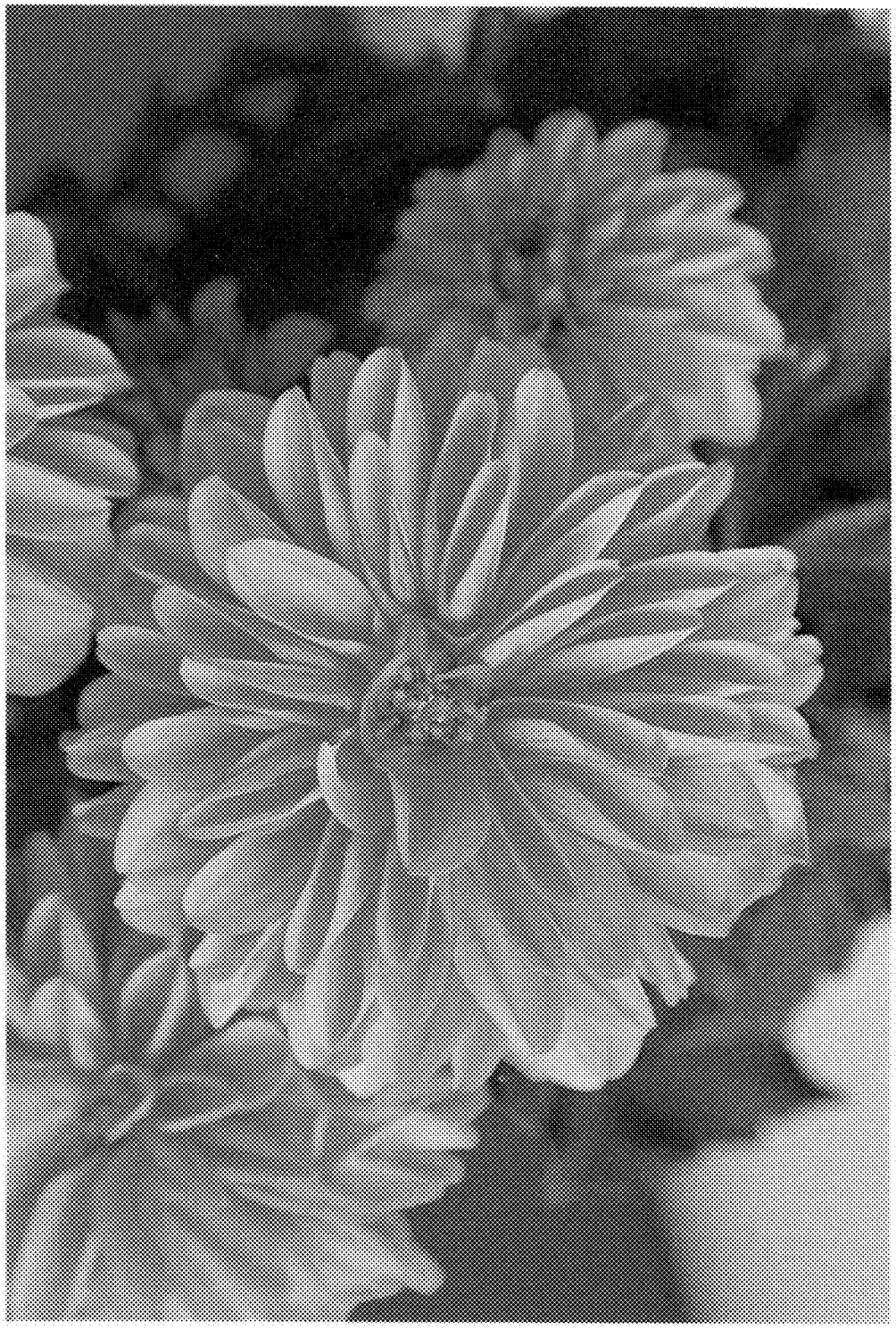

* * * * *